ns, Darby & Cushman

United States Patent [19]

Spencer et al.

[11] 4,172,856

[45] Oct. 30, 1979

[54] OLEFINS

[75] Inventors: Michael S. Spencer; Thomas V. Whittam, both of Stockton-on-Tees, England

[73] Assignee: Imperial Chemical Industries Limited, London, England

[21] Appl. No.: 903,042

[22] Filed: May 5, 1978

[51] Int. Cl.² .............................................. C07C 1/20
[52] U.S. Cl. ..................................... 585/640; 585/653
[58] Field of Search ............... 260/682, 683.15 R, 683

[56] References Cited

U.S. PATENT DOCUMENTS

| | | | |
|---|---|---|---|
| 4,021,502 | 5/1977 | Plank et al. | 260/683.15 R |
| 4,052,479 | 10/1977 | Chang et al. | 260/682 |
| 4,066,714 | 1/1978 | Rodewald | 260/682 |

*Primary Examiner*—C. Davis
*Attorney, Agent, or Firm*—Cushman, Darby & Cushman

[57] ABSTRACT

Olefins are produced by reacting a feedstock containing a hydrocarbon containing 2 or more carbon atoms in the molecule and/or a hydrocarbon derivative containing hydrogen-carbon links over a catalyst comprising "FU-1," which is a zeolite-like silica-containing material characterized inter alia by chemical composition and X-ray diffraction pattern. The feedstock is preferably methanol or dimethyl ether. The predominant olefin product can be controlled according to the reaction conditions used. Conversion to aromatics is very low.

10 Claims, No Drawings

OLEFINS

This invention relates to olefins and in particular to a process of making them by conversion of hydrocarbons and/or their derivatives in the presence of a silica-containing material as catalyst.

Olefins, especially ethylene and propylene, are used on a large scale as intermediates for the manufacture of staple products such as olefin polymers, ethylene oxide, non-ionic detergents, glycols and fibre-forming polyesters. Processes for producing olefins usually involve non-catalytic pyrolysis of volatile hydrocarbons such as natural gas liquids or petroleum distillates. Catalytic pyrolysis processes have been proposed but do not appear to have reached industrial use.

In countries where such volatile hydrocarbons are not to be used but such feedstocks as coal, oil shale and methane, and consequently carbon monoxide/hydrogen synthesis gas derived therefrom, are available, it would be desirable to produce olefins from synthesis gas. It has been proposed to do this by converting the synthesis gas to methanol or to hydrocarbons and/or their oxygenated derivatives and reacting such products over a zeolite of the ZSM-5 family. The reaction over such a zeolite is not entirely satisfactory because the olefins tend to react further to produce aromatic hydrocarbons, including polymethylated benzenes of limited usefulness. Better conversions to olefins can apparently be achieved by useing a modified catalyst and/or by careful temperature control, but such measures increase the complexity and cost of the process.

We have now found that our recently discovered silica-containing material "FU-1" can catalyse the conversion of such feedstocks to olefins with only slight formation of aromatic compounds.

The invention provides a process for making an olefin containing 6 or fewer carbon atoms in the molecule by reacting a feedstock comprising a hydrocarbon containing 2 or more carbon atoms in the molecule and/or a hydrocarbon derivative containing hydrogen-carbon links over a catalyst comprising the silica-containing material FU-1 as hereinafter defined and recovering the olefin from the product of the reaction.

FU-1 is a silica-containing material having the chemical composition 0.6 to 1.4$R_2O$. $Al_2O_3$. over 5 $SiO_2$. 0 to 40 $H_2O$ where R is a monovalent cation or $1/n$ of a cation of valency n and $H_2O$ is water of hydration additional to water notionally present when R is H and having an X-ray diffraction pattern including the following characteristic lines:

TABLE 1

| d (A) | 100 I/Io | d (A) | 100 I/Io |
|---|---|---|---|
| 9.51 | 31 | 4.48 | 6 |
| 8.35 | 8 | 4.35 | 13 |
| 6.92 | 28 | 4.07 | 19 |
| 6.61 | 9 | 4.00 | 9.4 |
| 6.26 | 9 | 3.89 | 13 |
| 5.25 | 16 | 3.73 | 28 |
| 4.61 | 63 | 3.68 | 3 |
|  |  | 3.44 | 100 |

Our co-pending UK application Nos. 46130/76—28267/77 (to be published as Netherlands application No. 7712173) corresponding to copending application Ser. No. 845,391, filed Oct. 25, 1977 in the name of Whittam describes FU-1 and its method of preparation in more detail. The silica to alumina ratio is typically in the range 10–300, especially 15–45.

In order to be useful to a preferred extent in the process of the invention FU-1 is converted from the form in which it is hydrothermally produced, in which form it contains the oxides of alkali metal and of the quaternary ammonium compound, to an active form by ion exchange of at least part of the ions represented by the alkali metal oxide and preferably also subjected to removal of at least part of the quaternary compound, for example, by calcination in air. The alkali metal compounds content of FU-1 as used in the process of the invention is preferably less than 4000, especially less than 500 ppm w/w calculated as equivalent $Na_2O$. The quaternary ammonium content is preferably less than 2% w/w calculated as elemental carbon. Preferably the FU-1 is activated by heating at 400°–600° C. in air or oxygen-free gas before beginning the reaction; such treatment is also suitable for re-activating used catalyst. The water content of freshly activated or reactivated catalyst is preferably 0 to 2 mols in the above chemical composition formula.

In the active form the alkali metal ions have been replaced at least partly by hydrogen or ions of polyvalent metals. Replacement by hydrogen can be effected by exchange with acid or with ions of ammonium or non-quaternary amine, since such ions decompose on calcination to leave hydrogen ions. The polyvalent metal is preferably selected from those having little or no catalytic activity for hydrogenation, except when synthesis is to accompany conversion, as described below. Suitable metals are from Group II or the rare earth group of the Periodic Table as set out in "Abridgments of Specifications" published by the UK Patent Office. Preferably hydrogen ions and polyvalent ions are both present. Calcium-hydrogen FU-1 appears to be especially selective for producing ethylene and propylene.

FU-1 may be used at full strength or in mixtures with diluent material such as inert silica, alumina or clay, a suitable proportion of diluent being in the range 10–40%. The diluent may facilitate forming FU-1 into shapes (such as 1–10 mm cylinders or spheres for use in a fixed bed or into fine particles for use in a fluidised bed) and also enables the rates of the wanted and unwanted reactions over it to be controlled. The diluent can, if desired, be a zeolite; a convenient combination is a mixture of FU-1 with a zeolite such as nu-1 or ZSM-4 or analcite, as synthesised together by suitable choice of conditions. Such a combination with nu-1 appears to be especially useful in making $C_2$ to $C_4$ olefins. (Nu-1 is described in our U.S. Pat. No. 4,060,590).

The feedstock can be for example a normally gaseous (up to $C_4$) hydrocarbon or mixture such as LPG or a readily vaporisable hydrocarbon or mixture ($C_5$ to $C_{12}$) such as natural gas liquids or naphtha or higher volatilisable hydrocarbons such as kerosene or gas oil. If it is a hydrocarbon derivative it is suitably one having at least 2 hydrogen atoms linked to at least some of its carbon atoms. Oxygenated hydrocarbons such as alcohols, ethers, carboxylic acids, esters, aldehydes and ketones and their acetals are very suitable feedstocks. An especially useful application of the process is the production of olefins from methanol and/or dimethyl ether, since FU-1, unlike for example the ZSM-5 family of zeolites, appears to be selective for the production of normally gaseous olefins and against the production of aromatic hydrocarbons. Crude feed and/or waste streams containing organic sulphur or nitrogen compounds can be upgraded to useful products by the process of the invention.

The products of reaction over FU-1 may include hydrocarbons other than the required olefins, as well as unwanted hydrocarbon derivatives and possibly also unconverted feedstock. The crude product is separated by condensation of the normally liquid compounds in it and the gaseous fraction is resolved by distillative fractionation or by adsorption. Unwanted and unreacted materials, after recovery of the required olefins and separation of products such as methane, carbon oxides, water and (when appropriate) hydrogen, can be subjected to further stages of conversion over FU-1 or recycled for further conversion with the main feedstock.

The reaction temperature is suitably in the range 300°–450°, especially 350°–400° C. when the product olefin is to contain 4 to 6 carbon atoms, but 400°–550° especially 425°–525° C. when ethylene and/or propylene are to be the main products.

The pressure at which the process is carried out is suitably in the range 1–50 atm. abs., especially 1–15 atm. abs., but higher pressures for example to to 300 atm. abs. can be used if convenient, for example as described below when synthesis is combined with the process of the invention.

The space velocity should be controlled so as to give the required product distribution. Thus, for example, when the feedstock is methanol, reaction at a liquid hourly space velocity of about 1.0 produces a higher proportion of dimethyl ether than when the space velocity is 0.2. The dimethyl ether can be recycled or reacted in a separate bed of FU-1 or other catalyst. It appears that the conversion of methanol is preferably incomplete, for example in the range 75–98%.

The catalyst maintains its activity for a substantial period, but can be regenerated by heating in the conditions preferably used for activating it. Very suitably it is used in the form of a fluidised bed and catalyst is continuously withdrawn, passed through a regeneration zone and returned to the olefin-forming reaction.

The process of the invention can be used in combination with a process of synthesis of hydrocarbons and/or oxygenated hydrocarbons by catalytic reaction of carbon oxides with hydrogen. Synthesis products can be separated before the reaction over FU-1 but, if desired, the FU-1 catalyst can be disposed so as to act on the synthesis products in advance of any product separation step, for example in a bed downstream of the synthesis catalyst, or by using a mixture of discrete pieces of synthesis catalyst and FU-1 catalyst, or by using discrete pieces made by shaping a mixture of powdered FU-1 and synthesis catalysts or by applying to FU-1 by impregnation or ion-exchange one or more compounds of metals or oxides having such synthesis activity. Suitable synthesis catalysts contain for example one or more of copper, zinc oxide, chromium oxide and the non-noble or noble metals from Group VIII of the Periodic Table. The pressure of the reaction over FU-1 can be chosen to suit the conditions of the synthesis reaction.

The following Examples 1, 2, 4 and 6 to 10 show the conversion of methanol to a gaseous product containing olefins. In each the gaseous product is cooled to condense out water, unconverted methanol and any oil and the gaseous fraction remaining is treated to separate dimethyl ether for recycle to the conversion and then to separate saturated hydrocarbons for use e.g. in generating part of the synthesis gas used to make the methanol. Note: in Examples 1 and 2 the composition of the total gaseous product is quoted, but in Examples 4 and 6–10 the dimethyl ether and carbon oxides have been separated and only the composition of the hydrocarbon fraction is quoted.

The term "LHSV" means volumes of liquid feed passing through unit volume of catalyst-filled space per hour. The symbols "TMA" and "Q" denote tetramethylammonium.

EXAMPLE 1

FU-1 catalyst preparation (moderate $Na_2O$)

A hydrothermal synthesis mixture having the composition $$12.6\ Na_2O.5.37\ (TMA)_2O.Al_2O_3.59.2\ SiO_2.3586\ H_2O$$

was made from 612 g of silica KS 300, 146.2 g of sodium hydroxide, 30.6 g of sodium aluminate 666.4 g of TMAOH solution and 10.46 liters of water. The mixture was reacted with stirring in a 25 liter stainless steel autoclave for 24 hours at 170° C. The solid product was collected on a filter, washed and dried overnight at 120° C. By X-ray diffraction it was shown to contain FU-1 as its major constituent with a slight trace of nu-1. Its composition was $$0.11\ Na_2O.1.07\ (TMA)_2O.Al_2O_3.20\ SiO_2.3.7\ H_2O.$$

This product was converted to a hydrogen form by refluxing for 5 hours with aqueous hydrochloric acid (2 ml of 5% w/w HCl per g FU-1), followed by filtering and washing, and then stirring for 1 hour at 50° C. with aqueous hydrochloric acid (3.65% w/w HCl, 12 ml per g FU-1), followed by filtering, washing and drying overnight at 120° C. The dried product was calcined at 450° C. for 17 hours in air and then had the composition $$0.04\ Na_2O.Al_2O_3.23.6\ SiO_2$$

and also contained 1.8% carbon and 0.4% nitrogen. ($Na_2O$ content 1600 ppm w/w). Product was pelleted by compression into 12×12 mm cylinders. A sample of these cylinders was crushed and a quantity of 3 mm fragments selected for test in methanol conversion.

Methanol conversion to $C_{4-6}$ olefins

A 10 ml charge (3.6 g) of the fragments was activated by calcination at 450° C. in air for 70 hours. Methanol vapour was passed over it at 380° C., atmospheric pressure and the gaseous and liquid products analysed (run A). Then the catalyst was re-activated and used in a second run (B) at 450° C. The results are shown in Table 2. It is evident that apart from dimethyl ether, the predominant products are butenes and pentenes, especially at the lower temperature.

TABLE 2

| Run No. | | A | B |
|---|---|---|---|
| Activation | | 450° C. 70h | 450° C. 2H |
| LHSV h$^{-1}$ | | 1.04 | 1.01 |
| Duration of run, minutes | | 30 | 60 |
| Temperature, °C. | | 380 | 450 |
| Gas Product | Vol, liters | 0.67 | 1.86 |
| Analysis % v/v | $C_6H_{12}$ | 1.5 | 1.0 |
| | $C_5H_{12}$ | 2.2 | — |

TABLE 2-continued

| Run No. | | A | B |
|---|---|---|---|
| | $C_5H_{10}$ | 14.6 | 5.3 |
| | $C_4H_{10}$ | 2.8 | 1.1 |
| | $C_4H_8$ | 10.8 | 7.4 |
| | $C_2,C_3$ | Under 2 | Under 2 |
| | $CH_4$ | 7.6 | 10.7 |
| | $CH_3OH$ | NIL | 7.8 |
| | $(CH_3)_2O$ | 59.7 | 65.8 |
| | $CO_2$ | 0.8 | 0.9 |
| Liquid Product | | | |
| Aqueous phase, vol, ml | | 1.3 | 3.7 |
| Composition % v/v $CH_3OH$ | | 8.0 | 30.0 |
| Oil phase, vol, ml | | 0.1 | 0.1 |

EXAMPLE 2

Preparation of FU-1/nu-1 mixture catalyst, low $Na_2O$

A hydrothermal synthesis mixture having the composition 12.64 $Na_2O.5.4$ $(TMA)_2O.Al_2O_3.59.3$ $SiO_2.3000$ $H_2O$ was made from 36 g of silica KS 300, 8.6 g of sodium hydroxide, 1.8 g of sodium aluminate, 39.3 g of TMAOH solution and 508 ml of water. A seed quantity (2.5 g) of nu-1 (low-D type) was stirred in. The whole mixture was reacted without agitation in a 1 liter Pyrex (RTM) liner in a 5 liter autoclave under 20 atm. pressure of nitrogen at 175° C. for 3 days. The solid phase was collected on a filter, washed and then dried overnight at 80° C. Its composition was 0.2 $Na_2O.1.3$ $(TMA)_2O.Al_2O_3.40$ $SiO_2.5$ $H_2O$.

By X-ray diffraction it was shown to contain 75% w/w of FU-1 and about 25% w/w of nu-1 (low-D type).

This product was converted to a hydrogen form via the ammonium form. First it was slurry-exchanged twice at 95° C. for 1 hour with 20 ml of 5% ammonium chloride per g flollowed by filtering, washing and finally drying at 110° C. overnight. A portion of the dried product was calcined in air at 450° C. for 17 hours and then had the following composition 0.01 $Na_2O$ (225 ppm w/w) $Al_2O_3.42.8$ $SiO_2$;

it also contained 3% w/w carbon and 0.6% w/w nitrogen. A sample of granules in the size range 1-3 mm was made by crushing the dried product and sieving it.

Conversion of methanol to low olefins

A 10 ml charge of these granules was activated by calcination as set out in column C of Table 3 and then used at atmospheric pressure to convert methanol at 380° C. (column C). After this run it was re-activated and used for a methanol conversion at a lower space velocity. Two further re-activations and conversions at 450° C. were carried out. Table 3 shows the activation conditions, space velocities and durations of the 4 runs, and also the product compositions. No liquid oily product was obtained. The gaseous products obtained at the lower space velocities were relatively rich in gaseous olefins. It is evident, by comparison with Example 1, that the change from pure FU-1 to the FU-1/nu-1 mixture and the decreased sodium oxide content have led to olefinic products of substantially lower average molecular weight.

TABLE 3

| Run No. | C | D | E | F |
|---|---|---|---|---|
| Activation | 450° C. | 450° C. | 500° C. | 500° C. |
| | 40h | 17h | 40h | 17h |
| LHSV $h^{-1}$ | 0.97 | 0.22 | 1.08 | 0.21 |
| Duration of run, minutes | 30 | 100 | 30 | 150 |
| Temperature, °C. | 380 | 380 | 450 | 450 |
| Gas Product | | | | |
| Total vol., liters | 0.65 | 0.63 | 1.08 | 1.01 |
| Composition % v/v | | | | |
| $C_{5+}$ | 0.2 | 5.3 | 1.9 | 2.3 |
| $C_4H_{10}$ | NIL | 6.0 | NIL | 1.1 |
| $C_4H_8$ | 1.1 | 10.0 | 2.1 | 3.6 |
| $C_3H_6$ | 2.6 | NIL | 1.5 | 6.1 |
| $C_2H_4$ | 3.1 | 8.2 | 1.7 | 4.0 |
| $H_2$ | 3.2 | 3.2 | 1.3 | 6.4 |
| $CH_4$ | NIL | 9.4 | 3.7 | 9.9 |
| $CH_3OH$ | 2.7 | NIL | 2.3 | 1.5 |
| $(CH_3)_2O$ | 87 | 46.7 | 84.7 | 64.6 |
| $CO_2$ | 0.5 | 1.9 | 0.8* | 0.8* |
| Liquid Product | | | | |
| Total vol, ml. | 1.2 | 0.9 | 1.3 | 1.2 |
| Composition % v/v | | | | |
| $CH_3OH$ | 25 | 23 | 29 | 25 |

*the carbon oxides fraction was mainly CO.

EXAMPLE 3

Conversion of n-hexane (run G)

The catalyst from the previous example was reactivated by calcining in air at 500° C. for 17 hours and then a n-hexane feed was introduced into the reactor instead of methanol. The LHSV was 1.0 $h^{-1}$ and the temperature 500° C. The products were as follows:

| Run time | 60 minutes | |
|---|---|---|
| Gas volume | 0.48 liters | |
| Gas Product % v/v | $C_{5+}$ | 4.4 |
| | $C_4H_{10}$ | 3.6 |
| | $C_4H_8$ | 6.0 |
| | $C_3H_8$ | 27.2 |
| | $C_3H_6$ | 35.9 |
| | $C_2H_6$ | 5.3 |
| | $C_2H_4$ | 2.0 |
| | $CH_4$ | 5.3 |
| | $H_2$ | 10.2 |
| Liquid Product, vol. | 8.8 ml. | |
| n-hexane | 99.5% | |
| remainder $C_4 - C_6$ isomers | | |

This catalyst gives a different cracking pattern from that of zeolites REY or HZSM-5 in that it yields negligible aromatisation, yet evidently catalytic cracking took place. The composition of the gaseous products shows that this process is potentially useful as a source of olefins.

EXAMPLE 4

Preparation of FU-1 catalyst

FU-1 was synthesised by reacting with stirring a mixture of composition

3$Na_2O.1.5$ $Q_2O.Al_2O_3.25$ $SiO_2.900$ $H_2O$ on the scale of 350 g of sodium aluminate at 180° C. for 12 hours. The tetramethylammonium was provided by the hydroxide. The silica source had the composition $Na_2O.0.15Al_2O_3.143$ $SiO_2.64$ $H_2O$ and was a sample of the material supplied by AKZO under the reference KS-300. Synthesis was carried out in presence of 170 g of seed FU-1. The synthesis product after filtration, washing and drying had the composition $$0.94\ Na_2O.1.5\ Q_2O.Al_2O_3.25.5\ SiO_2.6.4\ H_2O.$$

The hydrogen-form of this product was made by twice ion-exchanging by slurrying with 2 ml of 3.65% w/w HCl per g of solid for 1 hour at 90° C., filtering and washing. The washed material was dried overnight at 120° C. and then calcined at 450° C. for 48 hours in a stream (gas hourly space velocity 500) of air saturated with water at 25° C. The calcined material contained 0.8% w/w of carbon and had the composition $$0.06\ Na_2O.Al_2O_3.32.1\ SiO_2$$

on a carbon-free, water-free basis (1780 ppm $Na_2O$). It was formed into 3.2×3.2 mm cylindrical pellets by compression. (This preparation is described in more detail in Example 24 of our co-pending application referred to above).

Conversion of methanol to low olefins

Three 10 ml samples of these pellets were activated at 450° C. in air for 16 hours and tested by the procedure of Example 2. Table 4 shows results obtained at various temperatures and space velocities, some using catalyst (indicated by "r") reactivated by repeating the activation. The hydrocarbon percentages apply to the gaseous product after removal of non-hydrocarbon constituents such as dimethyl ether. The $C_4H_8$ fraction did not include any isobutene. Oil products were generally in trace quantities, exceptionally up to 2% w/w of the feed methanol.

TABLE 4

| Run No. | H | J | K | L | M | N | O | P | Q | R |
|---|---|---|---|---|---|---|---|---|---|---|
| Catalyst | fresh | fresh | r J | r K | fresh | r M | r N | r O | r P | r Q |
| LHSV, | 0.92 | 2.4 | 1.28 | 0.91 | 1.0 | 2.46 | 0.20 | 1.0 | 0.24 | 2.46 |
| Run time, min. | 60 | 25 | 47 | 66 | 60 | 24 | 300 | 60 | 250 | 25 |
| T, °C. | 450 | 500 | 500 | 450 | 450 | 450 | 450 | 500 | 500 | 500 |
| Hydrocarbons % v/v | | | | | | | | | | |
| $CH_4$ | 60.2 | 39.7 | 42.9 | 27.9 | 38.0 | 32.3 | 38.5 | 59.3 | 55.7 | 46.8 |
| $C_2H_6$ | 3.3 | 2.4 | 2.2 | 2.6 | 3.2 | 1.2 | 4.8 | 2.2 | 4.9 | 2.2 |
| $C_2H_4$ | 15.6 | 11.1 | 10.7 | 12.8 | 11.8 | 12.8 | 9.3 | 7.6 | 8.5 | 13.0 |
| $C_3H_8$ | 4.7 | 2.0 | 1.9 | 4.0 | 5.0 | 3.2 | 6.2 | 1.4 | 3.4 | 1.4 |
| $C_3H_6$ | 7.6 | 21.6 | 21.5 | 23.0 | 18.9 | 21.9 | 17.7 | 15.4 | 15.7 | 20.8 |
| $i-C_4H_{10}$ | 4.3 | 2.0 | 1.6 | 3.5 | 5.6 | 2.4 | 5.9 | 0.8 | 2.1 | 0.8 |
| $n-C_4H_{10}$ | 0.5 | 0.7 | 0.6 | 0.9 | 0.9 | 0.8 | 1.1 | 0.3 | 0.5 | 0.5 |
| $1-C_4H_8$ | 1.9 | 6.1 | 5.7 | 7.1 | 5.3 | 7.2 | 3.1 | 4.4 | 3.1 | 4.8 |
| $trans-2-C_4H_8$ | 0.5 | 8.1 | 7.3 | 9.7 | 5.3 | 10.0 | 6.5 | 4.8 | 3.1 | 5.3 |
| $cis-2-C_4H_8$ | 0.5 | 5.7 | 5.0 | 6.6 | 4.1 | 6.8 | 5.1 | 3.3 | 2.6 | 3.9 |
| $1,3-C_4H_6$ | 0.9 | 0.7 | 0.6 | 1.8 | 1.8 | 1.6 | 2.0 | 0.5 | 0.5 | 0.5 |
| Liquid product | | | | | | | | | | |
| Total vol, ml. | 3.1 | 3.3 | 3.9 | 3.3 | 3.8 | 3.8 | 3.3 | 3.4 | 1.6 | 4.1 |
| $CH_3OH$, % v/v | 13.5 | 22.0 | 17.5 | 21.0 | 10.5 | 26.3 | 13.5 | 21.2 | 10.3 | 35.0 |

EXAMPLE 5

Conversion of n-hexane

Fresh activated catalyst from Example 4 was used in the procedure of Example 2 at 450° C., LHSV 0.89 and then, after successive reactivations, at other temperature and space velocity combinations. The results are shown in Table 5. In each run the liquid product is essentially pure n-hexane, that is, there is no detectable aromatisation.

TABLE 5

| Run No. | S | T | U | V |
|---|---|---|---|---|
| Catalyst | fresh | r S | r T | r U |
| LHSV, | 0.89 | 0.89 | 2.6 | 0.21 |
| Duration of run, min. | 67 | 67 | 30 | 297 |
| Temperature, °C. | 450 | 500 | 500 | 500 |
| Gas Product | | | | |
| Hydrocarbons % v/v | | | | |
| $CH_4$ | 8.3 | 12.3 | 9.2 | 24.0 |
| $C_2H_6$ | 15.5 | 15.8 | 13.8 | 20.0 |
| $C_2H_4$ | 9.4 | 12.3 | 12.0 | 11.5 |
| $C_3H_8$ | 28.7 | 21.8 | 23.5 | 17.4 |
| $C_3H_6$ | 23.7 | 24.6 | 30.4 | 15.7 |
| $i-C_4H_{10}$ | 8.3 | 6.7 | 5.5 | 6.8 |
| $n-C_4H_{10}$ | 2.4 | 2.5 | 2.3 | 1.9 |
| $1-C_4H_8$ | 0.9 | 1.1 | 1.4 | 0.9 |
| $iso-C_4H_8$ | 0.6 | 0.4 | 0 | 0 |
| $trans-2-C_4H_8$ | 1.1 | 1.1 | 0.9 | 0.6 |
| $cis-2-C_4H_8$ | 0.6 | 0.7 | 0.5 | 0.4 |
| $1,3-C_4H_6$ | 0.6 | 0.7 | 0.5 | 0.6 |
| Liquid product | | | | |
| Total vol, ml. | 8.0 | 6.6 | 7.6 | 5.2 |

EXAMPLE 6

Rare-earth hydrogen FU-1

In a repeat of the synthesis described in Example 4 an FU-1 of composition $$0.8\ Na_2O.1.5\ Q_2O.Al_2O_3.24\ SiO_2.8.6\ H_2O$$

was obtained. This was converted to the hydrogen form by once slurrying with 2 ml of 5% w/w HCl per g of solid for 1 hour at 90° C., filtering and washing and was then dried overnight at 100° C. and calcined as before. The calcined product contained 0.2% w/w of carbon and had the composition $$0.09\ Na_2O.Al_2O_3.23.8\ SiO_2$$

on a carbon-free, water-free basis. It was converted to rare earth form by once slurrying with 3 ml of 10% RE $Cl_3.6H_2O$ solution initially at pH 3 for 1 hour at 90° C., filtering and washing, and then dried overnight at 100° C. and calcined at 450° C. for 6 hours. The calcined product contained 0.1% w/w of carbon and had the composition $$0.07\ Na_2O.0.14\ RE_2O_3.Al_2O_3.24.3\ SiO_2$$

on a carbon-free, water-free basis. (The $Na_2O$ content is 2800 ppm w/w). ($RE\ Cl_3$ signified a mixture of chlorides of rare earth metals derived from an oxide mixture having the weight percentage composition Ce 45 as Ce $O_2$, La 23 as $La_2O_3$, Nd 16 as $Nd_2O_3$, Pr 10 as $Pr_2O_3$, Sm 4 as $Sm_2O_3$ and Gd 2.5 as $Gd_2O_3$).

The calcined product was formed into 3.2×3.2 mm cylindrical pellets by compression.

Table 6 shows results of testing these pellets in the conversion of methanol by the procedure of Example 2. Oil product was under 1% w/w of the feed in run W and undetectable in run X. Operation at 450° C. is evidently preferable for olefin production to operation at 600° C. In view of the loss of catalyst activity with time, adaptation of the process to fluidised bed operation would be desirable.

TABLE 6

| Run No. | W | | | X | |
|---|---|---|---|---|---|
| LHSV, | 1.0 | | | 1.0 | |
| Temperature, °C. | 450 | | | 600 | |
| Run time, min | 0–20 | 20–40 | 40–60 | 0–22 | 22–42 |
| Gas product | | | | | |
| Vol hydrocarbon, ml. | 530 | 80 | 55 | 490 | 402 |
| Composition, % v/v | | | | | |
| $CH_4$ | 29.3 | 47.1 | 55.7 | 74.8 | 93.0 |
| $C_2H_6$ | 2.0 | 1.3 | 1.0 | 0.9 | 2.1 |
| $C_2H_4$ | 10.9 | 11.4 | 11.9 | 6.8 | 3.4 |
| $C_3H_8$ | 2.7 | 0.7 | 0 | <0.2 | 0 |
| $C_3H_6$ | 20.8 | 18.9 | 16.9 | 11.1 | <0.3 |
| $i$-$C_4H_{10}$ | 1.9 | 0.7 | <1 | 0 | 0 |
| $n$-$C_4H_{10}$ | 0.9 | 0 | <1 | 0 | 0 |
| $l$-$C_4H_8$ | 8.5 | 5.4 | 4.0 | 2.2 | 0.5 |
| iso-$C_4H_8$ | 4.3 | 1.3 | 1.0 | 0.5 | <0.3 |
| trans-2-$C_4H_8$ | 10.5 | 7.4 | 5.0 | 1.8 | 0.5 |
| cis-2-$C_4H_8$ | 6.9 | 4.7 | 4.0 | 1.2 | 0.3 |
| 1,3-$C_4H_6$ | 1.4 | 1.0 | 0.5 | 0.8 | 0.2 |
| Liquid product | | | | | |
| Total vol, ml. | 0.9 | 1.7 | 1.6 | 0.8 | 1.2 |
| Composition % v/v | | | | | |
| $CH_3OH$ | 3.7 | 27.8 | 45.5 | 3.7 | 20.0 |

EXAMPLE 7

Methanol conversion with graded temperature

Methanol vapour was passed over a first 10 ml bed at 450° C. and the products leaving that bed were passed over a second 10 ml bed at 560° C. The catalyst in each bed was a sample of the pellets of RE—H—FU-1 as used in Example 6. The LHSV in each bed was $1.0\ h^{-1}$. Table 7 shows the volumes and compositions of products collected in three successive run periods. There were traces of an oil product only in the third period. Again there are favourable yields of ethylene and propylene in the first 20 minutes and fluidised bed operation with frequent or continuous catalyst renewal would be advantageous.

TABLE 7

| Run period, min | 0–20 | 20–40 | 40–60 |
|---|---|---|---|
| Gas product | | | |
| Vol. hydrocarbon, ml | 462 | 510 | 522 |
| Composition % v/v | | | |
| $CH_4$ | 31.5 | 63.9 | 81.6 |
| $C_2H_6$ | 2.3 | 1.6 | 1.8 |
| $C_2H_4$ | 15.3 | 8.9 | 5.0 |
| $C_3H_8$ | 2.5 | 0.5 | <0.3 |
| $C_3H_6$ | 25.2 | 14.8 | 8.0 |
| $i$-$C_4H_{10}$ | 2.0 | 0.2 | 0 |
| $n$-$C_4H_{10}$ | 0.7 | 0.1 | 0 |
| $l$-$C_4H_8$ | 5.5 | 2.7 | 1.3 |
| iso-$C_4H_8$ | 5.7 | 0.9 | 0.3 |
| trans-2-$C_4H_8$ | 4.8 | 2.3 | 1.0 |
| cis-2-$C_4H_8$ | 3.3 | 1.6 | 0.8 |
| 1,3-$C_4H_6$ | 1.2 | 0.9 | 0.4 |
| Liquid product | | | |
| Total vol, ml | 1.0 | 1.4 | 1.6 |
| Composition, % v/v | | | |
| $CH_3OH$ | 0 | 0.2 | 17.2 |

EXAMPLE 8

Activation and reactivation in absence of oxygen: H—FU-1

In a micro-reactor a charge (0.2177 g) of the catalyst pellets made as described in Example 4 was treated as follows:

(i) activated in fast-flowing nitrogen at 5.6 atm. abs. pressure, 450° C. for 1 hour;
(ii) 0.6 microliters of methanol were injected into the nitrogen and and the outlet gas was analysed for hydrocarbons;
(iii) the temperature was increased to 475° C., 0.6 microliters of n-hexane were injected into the nitrogen and the outlet gas was analysed for hydrocarbon;
(iv) the catalyst was aged by injecting 10 successive methanol portions each of 10 microliters into the nitrogen;
(v) the temperature was decreased to 450° C. and activation repeated as in step (i);
(vi) step (ii) was repeated;
(vii) step (iii) was repeated.

The results are shown in Table 8. It appears that ageing and then reactivation in nitrogen has a potentially favourable effect on the olefin content of the products.

TABLE 8

| Reactant | $CH_3OH$ | | $C_6H_{14}$ | |
|---|---|---|---|---|
| Temperature, °C. | 450 | | 475 | |
| Catalyst condition | Fresh | Aged | Fresh | Aged |
| Step | ii | vi | iii | vii |
| Hydrocarbons, % v/v | | | | |
| $CH_4$ | 6.9 | 6.0 | 1.8 | 1.8 |
| $C_2H_6$ | 1.2 | 1.1 | 6.7 | 10.3 |
| $C_2H_4$ | 10.7 | 19.6 | 7.5 | 5.4 |
| $C_3H_8$ | 13.6 | 3.8 | 28.4 | 21.2 |
| $C_3H_6$ | 18.9 | 20.8 | 26.0 | 32.9 |
| $i$-$C_4H_{10}$ | 19.9 | 19.0 | 1.9 | 5.6 |
| $n$-$C_4H_{10}$ | 5.8 | 2.2 | 6.7 | 5.1 |
| $l$-$C_4H_8$ | 1.9 | 2.8 | 1.7 | 2.7 |
| iso-$C_4H_8$ | 5.5 | 7.8 | 4.3 | 6.4 |
| trans-2-$C_4H_8$ | 3.2 | 4.5 | 2.6 | 4.0 |
| cis-2-$C_4H_8$ | 2.9 | 4.2 | 2.3 | 4.6 |
| 1,3-$C_4H_6$ | 9.6 | 8.1 | 2.1 | 0 |

EXAMPLE 9

Activation and reactivation in absence of oxygen: RE—H—FU-1

Example 8 was repeated using 0.1342 g of the catalyst prepared in example 6. The results are given in table 9. Again ageing and then reactivation in nitrogen have a potentially favourable effect, especially on the production of ethylene and propylene.

TABLE 9

| Reactant | $CH_3OH$ | | $C_6H_{14}$ | |
|---|---|---|---|---|
| Temperature, °C. | 450 | | 475 | |
| Catalyst condition | Fresh | Aged | Fresh | Aged |
| Step | ii | vi | iii | vii |
| Hydrocarbons, % v/v | | | | |
| $CH_4$ | 6.7 | 9.5 | 1.9 | 2.2 |
| $C_2H_6$ | 1.0 | 0.4 | 9.4 | 12.3 |

TABLE 9-continued

| Reactant | CH3OH | | C6H14 | |
|---|---|---|---|---|
| Temperature, °C. | 450 | | 475 | |
| Catalyst condition | Fresh | Aged | Fresh | Aged |
| Step | ii | vi | iii | vii |
| C2H4 | 13.2 | 15.8 | 4.9 | 4.6 |
| C3H8 | 10.7 | 6.4 | 18.7 | 17.4 |
| C3H6 | 23.7 | 27.5 | 37.8 | 44.8 |
| i-C4H10 | 11.0 | 4.3 | 2.6 | 1.6 |
| n-C4H10 | 5.6 | 1.7 | 5.1 | 4.4 |
| l-C4H8 | 3.2 | 4.6 | 3.5 | 4.3 |
| iso-C4H8 | 8.5 | 11.2 | 7.3 | 6.8 |
| trans-2-C4H8 | 5.0 | 7.1 | 4.8 | 1.6 |
| cis-2-C4H8 | 5.0 | 11.6 | 4.1 | 0 |
| 1,3-C4H6 | 6.6 | | 0 | 0 |

EXAMPLE 10

Calcium hydrogen FU-1

In a repeat on the scale of 550 g of sodium aluminate of the synthesis described in Example 1 of our co-pending application an FU-1 of composition 0.55 Na2O.1.6 Q2O.Al2O3.34.7 SiO2.7 H2O was produced. This was converted to the calcined hydrogen form by the method described in Example 6 above and then contained 0.3% carbon and had the composition 0.03 Na2O.Al2O3.33.8 SiO2.

on a carbon-free, water-free basis. (The Na2O content is 850 ppm w/w). This product was slurried at 90° C. for 1 hour in a calcium chloride solution (140 g/l) using 3 ml of solution per g of H—FU-1. The resulting Ca—H—FU-1 was washed, dried overnight at 100° C. and calcined for 6 hours at 450° C. It then contained 0.2% w/w of carbon and had the composition 0.01 Na2O.0.58 CaO.Al2O3.33.6 SiO2 on a carbon-free, water-free basis. (The Na2O content is 280 ppm w/w).

Cylindrical pellets 3.2×3.2 mm were formed from it by dry compression.

Activity test

A sample (0.4377 g) of these pellets was charged to a micro reactor, and subjected to steps (i), (ii) and (iii) described in Example 8. The results are shown in Table 10. It is evident that Ca—H—FU-1 has considerable selectivity towards the formation of ethylene and propylene, both from methanol and from n-hexane.

TABLE 10

| Reactant | CH3OH | n-hexane |
|---|---|---|
| Temperature, °C. | 450 | 475 |
| Hydrocarbons % v/v | | |
| CH4 | 6.2 | 2.3 |
| C2H6 | 1.8 | 12.8 |
| C2H4 | 19.3 | 7.5 |
| C3H8 | 13.6 | 16.0 |
| C3H6 | 42.9 | 55.3 |
| i-C4H10 | 0 | |
| n-C4H10 | 0 | 2.9 |
| l-C4H8 | 3.3 | 4.9 |
| iso-C4H8 | 2.5 | 0 |
| trans-2-C4H8 | 4.7 | 0 |
| cis-2-C4H8 | 5.1 | 0 |
| 1,3-C4H6 | 0 | 0 |

EXAMPLE 11

Dimethyl ether conversion

Example 8 was repeated but with dimethyl ether feed. The conversion to hydrocarbons was higher than with methanol feed, but the product distribution (shown in table 11) was similar.

TABLE 11

| Catalyst condition | Fresh | Aged |
|---|---|---|
| Hydrocarbons % v/v | | |
| CH4 | 5.6 | 5.3 |
| C2H6 | 1.1 | 0.9 |
| C2H4 | 9.0 | 9.6 |
| C3H8 | 13.0 | 7.5 |
| C3H6 | 17.0 | 18.8 |
| i-C4H10 | 22.7 | 22.7 |
| n-C4H10 | 7.3 | 2.6 |
| l-C4H8 | 2.0 | 3.5 |
| iso-C4H8 | 5.0 | 7.2 |
| trans-2-C4H8 | 3.2 | 4.7 |
| cis-2-C4H8 | 2.7 | 4.3 |
| C4H6 | 11.5 | 12.8 |

We claim:

1. A process for making an olefin containing 6 or fewer carbon atoms in the molecule which comprises reacting a feedstock comprising a volatilizable hydrocarbon containing 2 or more carbon atoms in the molecule and/or a hydrocarbon derivative containing hydrogen-carbon links over a catalyst comprising the silica-containing material FU-1 having the chemical composition 0.6 to 1.4 R2O.Al2O3. over 5 SiO2.0 to 40 H2O where R is a monovalent cation or 1/n of a cation of valency n, and having an X-ray pattern including the following characteristic lines:

| d (A) | 100 I/Io | d (A) | 100 I/Io |
|---|---|---|---|
| 9.51 | 31 | 4.48 | 6 |
| 8.35 | 8 | 4.35 | 13 |
| 6.92 | 28 | 4.07 | 19 |
| 6.61 | 9 | 4.00 | 9.4 |
| 6.26 | 9 | 3.89 | 13 |
| 5.25 | 16 | 3.73 | 28 |
| 4.61 | 63 | 3.68 | 3 |
| | | 3.44 | 100 |

2. A process according to claim 1 in which the FU-1 contains less than 500 ppm w/w of alkali metal compounds calculated as equivalent Na2O.

3. A process according to claim 1 in which the FU-1 contains less than 2% w/w of quaternary ammonium compound calculated as elementary carbon.

4. A process according to claim 1 in which the catalyst contains the calcium-hydrogen form of FU-1.

5. A process according to claim 1 in which the feedstock is a normally gaseous or a volatilisable hydrocarbon.

6. A process according to claim 1 in which the feedstock is an oxygenated hydrocarbon.

7. A process according to claim 6 in which the feedstock is methanol.

8. A process according to claim 1 in which the reaction temperature is in the range 350–400° C. when the product olefin is to contain 4 to 6 carbon atoms or 425–525° C. when ethylene and/or propylene are to be the main products.

9. A process according to claim 6 in which the reaction product is treated to separate methane, carbon oxides, water and any hydrogen and to recover the required olefin or olefins, and in which unwanted other products are at least partly recycled to the reaction.

10. A process according to claim 1 in combination with a process of synthesis of hydrocarbons and/or oxygenated hydrocarbons by catalytic reaction of carbon oxides with hydrogen, the FU-1 catalyst being disposed so as to act on the synthesis products.

* * * * *